(12) United States Patent
Omidbakhsh

(10) Patent No.: US 8,865,196 B2
(45) Date of Patent: Oct. 21, 2014

(54) ANTIMICROBIAL COMPOSITIONS

(75) Inventor: Navid Omidbakhsh, Mississauga (CA)

(73) Assignee: Virox Technologies Inc., Oakville, Ontario (CA)

( * ) Notice: Subject to any disclaimer, the term of this patent is extended or adjusted under 35 U.S.C. 154(b) by 173 days.

(21) Appl. No.: 12/673,391

(22) PCT Filed: Aug. 15, 2008

(86) PCT No.: PCT/CA2008/001471
§ 371 (c)(1),
(2), (4) Date: Feb. 12, 2010

(87) PCT Pub. No.: WO2009/021336
PCT Pub. Date: Feb. 19, 2009

(65) Prior Publication Data
US 2011/0182958 A1     Jul. 28, 2011

Related U.S. Application Data

(60) Provisional application No. 60/955,991, filed on Aug. 15, 2007.

(51) Int. Cl.
| A01N 39/00 | (2006.01) |
| A01P 3/00 | (2006.01) |
| A01P 1/00 | (2006.01) |
| A01N 25/02 | (2006.01) |
| A01N 25/30 | (2006.01) |
| A01N 37/36 | (2006.01) |
| A01N 59/00 | (2006.01) |
| A01N 31/04 | (2006.01) |

(52) U.S. Cl.
CPC ............... *A01N 37/36* (2013.01); *A01N 25/30* (2013.01); *A01N 31/04* (2013.01); *A01N 59/00* (2013.01)
USPC ......................................... 424/405; 424/616

(58) Field of Classification Search
CPC ....... A01N 37/36; A01N 31/04; A01N 25/30; A01N 59/00; A01N 424/616
See application file for complete search history.

(56) References Cited

U.S. PATENT DOCUMENTS

| 4,717,737 | A | * | 1/1988 | Kern ............................. 514/547 |
| 5,728,666 | A |   | 3/1998 | Vitomir |
| 6,165,957 | A | * | 12/2000 | Vitomir ......................... 510/203 |
| 6,296,880 | B1 |   | 10/2001 | Murad |
| 6,383,523 | B1 |   | 5/2002 | Murad |
| 6,465,405 | B1 | * | 10/2002 | Vitomir ......................... 510/206 |
| 6,593,283 | B2 |   | 7/2003 | Hei et al. |
| 6,927,237 | B2 |   | 8/2005 | Hei et al. |
| 7,632,523 | B2 | * | 12/2009 | Ramirez et al. ................ 424/616 |
| 2002/0072288 | A1 |   | 6/2002 | Hei et al. |
| 2002/0155969 | A1 | * | 10/2002 | Rees et al. ..................... 510/384 |
| 2003/0161891 | A1 |   | 8/2003 | Ruiter |
| 2003/0181377 | A1 |   | 9/2003 | Hallahan et al. |
| 2003/0203035 | A1 |   | 10/2003 | Hasan et al. |
| 2003/0206965 | A1 |   | 11/2003 | Hasan et al. |
| 2003/0228996 | A1 |   | 12/2003 | Hei et al. |
| 2004/0033923 | A1 |   | 2/2004 | McClung |
| 2004/0137077 | A1 |   | 7/2004 | Ancira et al. |
| 2004/0171687 | A1 |   | 9/2004 | Kemp et al. |
| 2004/0182793 | A1 |   | 9/2004 | Owens |
| 2005/0058719 | A1 |   | 3/2005 | Ramirez et al. |
| 2005/0133460 | A1 |   | 6/2005 | McClung |
| 2005/0145824 | A1 |   | 7/2005 | McClung |
| 2005/0145825 | A1 |   | 7/2005 | McClung |
| 2005/0145826 | A1 |   | 7/2005 | McClung |
| 2005/0255172 | A1 |   | 11/2005 | Omidbakhsh |
| 2006/0172911 | A1 |   | 8/2006 | McClung |

FOREIGN PATENT DOCUMENTS

| CA | 2 475 327 A1 | 8/2003 |
| CA | 2 503 627 A1 | 6/2004 |
| EP | 1 388 575 | 2/2004 |
| WO | WO 99/52360 | 10/1999 |
| WO | 2004/035718 | 4/2004 |

OTHER PUBLICATIONS

Bio-Soft® S-101, Stepan (2012) downloaded from http://www.stepan.com/templates/product.aspx?id=2375, Oct. 10, 2013.*

* cited by examiner

*Primary Examiner* — Kortney L Klinkel
*Assistant Examiner* — Lisbeth C Robinson
(74) *Attorney, Agent, or Firm* — Clark & Brody

(57) ABSTRACT

An environmentally- and user-friendly, aqueous antimicrobial solution comprising effective amounts of hydrogen peroxide, glycolic acid, and at least one antimicrobially-active solvent chosen from benzyl alcohol and phenoxyethanol; concentrated versions of same; kits that can be used to make same; wipes containing same; and the use of same in a method of antimicrobial treatment of a surface contaminated with a microorganism (e.g. bacterial or fungal spore such as *C. Difficile*).

11 Claims, No Drawings

ANTIMICROBIAL COMPOSITIONS

The present application claims priority from U.S. provisional patent application 60/955,991, filed Aug. 15, 2007, which is hereby incorporated by reference in its entirety.

FIELD OF THE INVENTION

This invention relates to antimicrobial compositions.

BACKGROUND OF THE INVENTION

There is, at present, an ongoing need for antimicrobial compositions that are effective against a wide range of microorganisms while, at the same time, are environmentally- and user-friendly. The specific requirements for such compositions vary according to the intended application (e.g. sanitizer, disinfectant, sterilant, sporicide, etc.) and applicable public health requirements. For example, as set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2), a sanitizer should provide a 99.999% reduction (5-log order reduction) within 30 seconds at room temperature, 20±2° C., against several test organisms.

Prior art antimicrobial compositions are disclosed in the following published U.S. patent applications and issued U.S. patents:

| | |
|---|---|
| 2006/0172911 | McClung |
| 2005/0255172 | Omidbakhsh |
| 2005/0145826 | McClung |
| 2005/0145825 | McClung |
| 2005/0145824 | McClung |
| 2005/0133460 | McClung |
| 2005/0058719 | Ramirez et al |
| 2004/0182793 | Owens |
| 2004/0171687 | Kemp et al. |
| 2004/0137077 | Ancira et al. |
| 2004/0033923 | McClung |
| 2003/0206965 | Hasan et al. |
| 2003/0203035 | Hasan et al. |
| 2003/0228996 | Hei et al. |
| 2003/0181377 | Ramirez et al. |
| 2003/0161891 | Ruiter |
| 2002/0072288 | Hei et al. |
| 6,927,237 | Hei et al. |
| 6,593,283 | Hei et al. |
| 6,383,523 | Murad |
| 6,296,880 | Murad |

Notwithstanding the existence of many different prior art antimicrobial compositions, the present invention is intended to provide new environmentally- and user-friendly compositions that are effective against many different microorganisms, at reasonably short contact times, including compositions that are effective against bacterial and fungal spores (e.g. *Clostridium Difficile*, or *C. Difficile*) that are notoriously difficult to kill with known antimicrobial agents.

SUMMARY OF THE INVENTION

The invention provides, in accordance with a first aspect, an antimicrobial solution comprising:
a. an effective amount of hydrogen peroxide;
b. an effective amount of glycolic acid; and
c. an effective amount of at least one antimicrobially-active solvent chosen from benzyl alcohol and phenoxyethanol.

In accordance with a second aspect, the invention provides an antimicrobial solution consisting essentially of:
a. an effective amount of hydrogen peroxide;
b. an effective amount of glycolic acid; and
c. an effective amount of at least one antimicrobially-active solvent chosen from benzyl alcohol and phenoxyethanol.

In accordance with additional aspects of the invention, the invention provides concentrated versions of the solution, solutions that are effective against bacterial and fungal spores, kits that can be used to make the solution, wipes in which are embedded the solution, the use of the solution in a method of antimicrobial treatment of a surface contaminated with a microorganism, and viscous embodiments of the solution that maintain their viscosity over time.

The invention will be better understood with reference to the following detailed description of embodiments of the invention.

DETAILED DESCRIPTION OF EMBODIMENTS OF THE INVENTION

In this specification (description and claims), the following terms have the following meanings.

The term "composition" is used generally to mean a substance regardless of its form, and includes a solution, a dry particulate formulation, and a combination of one or more solutions and one or more dry particulate formulations such as may be contained in a kit.

The term "comprising," when used in relation to a number of integers or elements, means including without being limited to the recited integers or elements. The term "consisting essentially of" means including the recited integers or elements (and normal impurities present therein) and such additional integers or elements that do not materially affect the basic and novel properties of the invention. "Basic and novel properties of the invention" means the antimicrobial properties of the invention. "Antimicrobial properties" is a broad term that encompasses but is not restricted to sporicidal properties. The term "consisting of" means including only the recited integers or elements and no additional integers or elements, except those that may be present as normal impurities.

The expression "% w/w" means the percentage by weight, relative to the weight of the total composition, unless otherwise specified.

Numeric ranges recited herein include the upper and lower limits of the ranges, unless otherwise specified.

"Sporicide" means a composition that can kill/inactivate bacterial or fungal endospores under the conditions specified in and to the degree required by quantitative carrier test method ASTM E2111, entitled "Standard Quantitative Carrier Test Method to Evaluate the Bactericidal, Fungicidal, Mycobactericidal and Sporicidal Potencies of Liquid Chemical Germicides."

"Antimicrobial composition" is used generally herein to specify a composition having disinfecting activity. Thus, the term is used to include compositions that are sanitizers, disinfectants, sporicides and/or sterilants.

Because one or more definitions relating to antimicrobial activity contained herein may be different from definitions used in some governmental regulations, the use of such definitions herein is not intended to indicate compliance with any particular governmental standard for antimicrobial activity.

"Hydrogen peroxide releasing component" means any component which produces hydrogen peroxide when the component is in contact with water. Suitable water-soluble sources of hydrogen peroxide for use herein include percarbonates, persilicates, persulphates (such as monopersulfate), perborates and mixtures thereof. In addition, the term encompasses other classes of peroxides including dialkyl peroxides, diacylperoxides, organic and inorganic peroxides and/or hydroperoxides. The solutions of the invention can be formulated and sold in ready-to-use or concentrated formats. Concentrated versions of the solution can be used full-strength. However, typically they will be diluted with a solvent (e.g. water) prior to use.

The ingredients of the solution can be sold as separate components contained in a kit and combined by the end user, optionally by adding a solvent (e.g. water), to form a solution according to the invention. The person skilled in the art will appreciate that all ingredients, except for benzyl alcohol and phenoxyethanol, are available in either dry or liquid forms. The solvents are available only in liquid form. The kit may contain suitable directions for carrying out the method of the invention (described below) and may include recommended dilution ratios, applications, other application techniques and safety warnings.

Solutions according to the invention may be embedded in wipes for convenient application. By "wipes" is meant a textile medium (e.g. towel) that is disposed of after single or multiple uses. Preferably, the wipes are packaged in a plastic box or container.

In a ready-to-use solution according to the invention, the solution comprises hydrogen peroxide in a concentration of from 3, 3.5, 4, 4.5, 5.0, 5.5, 6.0, 6.5, 7, or 7.5% w/w and less than 8, 7, or 5% w/w. In certain embodiments, the hydrogen peroxide concentration is from 3 to 8% w/w, 3 to 7% w/w, or from 4 to 7% w/w.

The concentration of glycolic acid is from 0.1, 0.5, 0.6, 0.7, 0.8, 0.9, 1, 1.1, 1.2, 1.3, 1.4, or 1.5% w/w and less than 6, 5, 2, or 1.5% w/w. In certain embodiments, the glycolic acid is present in a concentration of from 0.1 to 6% w/w, 0.1 to 5% w/w, 0.5 to 5% w/w, 0.75 to 2% w/w, or from 1 to 1.5% w/w.

Furthermore, the concentration of the antimicrobially-active solvent is from 1, 2, or 2.5 and less than 5, 4, 3.5, or 3, % w/w. In certain embodiments, the solution comprises benzyl alcohol in a concentration of from 0.1 to 5% w/w, 1 to 5% w/w, 2 to 5% w/w, 2 to 4% w/w, or from 3 to 4 w/w %. In another embodiment, the benzyl alcohol is present in a concentration of less than 4% w/w.

Compositions according to the present invention may further comprise effective amounts of additional ingredients to improve certain properties or impart selected characteristics. For example, the compositions may comprise an effective amount of at least one surfactant to help solubilize certain ingredients in compositions or solutions according to the invention (e.g. benzyl alcohol) and/or to impart cleaning properties. The compositions may further comprise a hydrogen peroxide stabilizer or chelating agent to maintain the level of hydrogen peroxide or hydrogen peroxide releasing component over time. Thickening agents that are compatible with hydrogen peroxide (i.e. which do not break down and lose their thickening properties in the presence of hydrogen peroxide) may also be added. pH adjusters and buffering agents (e.g. NaOH, KOH, HCl, phosphoric acid, citric acid) may be added to achieve or maintain the desired pH.

Other ingredients that may be included are skin conditioning agents or emollients, builders, fragrances, dyes, corrosion inhibitors, additional antimicrobial agents (e.g. benzoic acid, salicylic acid, alcohols having from 1 to 6 carbons, quaternary ammonium compounds, essential oils, and phenolic compounds), additional solvents, radical scavengers, soil suspenders, dye transfer agents, and dispersants. The nature and amount of such additional ingredients will be apparent to the person skilled in the art, having regard to prior art publications such International Publication No. WO 99/52360 to Serego Allighieri et al.

The surfactant can be selected from any anionic, cationic, nonionic, and amphoteric surfactants that are known in the art to have cleaning, detersive or solubilizing properties.

Non-limiting examples of anionic surfactants useful in the present invention are $C_8$ to $C_{16}$ alkyl aryl sulfonic acids and alkali metal, ammonium, calcium and magnesium salts thereof, sulfonated $C_{12}$ to $C_{22}$ carboxylic acids and alkali metal, ammonium, calcium and magnesium salts thereof, $C_6$ to $C_{22}$ alkyl diphenyl oxide sulfonic acids and alkali metal, ammonium, calcium and magnesium salts thereof, naphthalene sulfonic acids and alkali metal, ammonium, calcium and magnesium salts thereof, $C_8$ to $C_{22}$ alkyl sulfonic acids and alkali metal, ammonium, calcium and magnesium salts thereof, alkali metal, ammonium, calcium and magnesium $C_8$ to $C_{18}$ alkyl sulfates, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof. Other suitable anionic surfactants that can be used herein are described in "Surface Active Agents and Detergents" (Vol. I and II by Schwartz, Perry and Berch).

The anionic surfactant may be chosen from $C_8$ to $C_{16}$ alkyl aryl sulfonic acids and alkali metal, ammonium, calcium and magnesium salts thereof (e.g. dodecyl benzene sulfonic acid and its sodium salt), $C_6$ to $C_{22}$ alkyl diphenyl oxide sulfonic acids and alkali metal, ammonium, calcium and magnesium salts thereof, and mixtures thereof.

Suitable cationic surfactants for use herein are quaternary ammonium compounds containing alkyl or substituted alkyl groups, alkyl amide and carboxylic acid groups, ether groups, unsaturated alkyl groups, and cyclic quaternary ammonium compounds, which can be chlorides, dichlorides, bromides, methylsulphates, chlorophenates, cyclohexylsulphamates or salts of the other acids. Among the possible cyclic quaternary ammonium compounds are the following: alkylpyridinium chlorides and/or sulphates, the alkyl group may be cetyl, dodecyl or hexadecyl group, alkylisoquinolyl chlorides and/or bromides, the alkyl group may be a dodecyl group. Particularly suitable quaternary ammonium compounds for use herein include alkyl dimethyl benzyl ammonium chloride, octyl decyl dimethyl ammonium chloride, dioctyl dimethyl ammonium chloride, didecyl dimethyl ammonium chloride, alkyl dimethyl ammonium saccharinate, cetylpyridinium and mixtures thereof. Non-limiting examples of amphoteric surfactants are imidazoline derivatives (e.g. alkylamphoacetates, alkylamphopropionates, and alkyliminopropionates), alkylbetaines, alkylamidopropylbetaines, alkylsulfobetaines, amine oxides and mixtures thereof.

Non-limiting examples of non-ionic surfactants are alkylarylpolyether alcohols having degrees of ethoxylation from 1.5 to 120, linear polyether alcohols having an alkyl chain length from between about 4 and 22 carbons, mixed linear alcohol ethoxylates, secondary alcohol ethoxylates having an alkyl chain length from between about 6 and 22 carbons, branched alkyl alcohol ethoxylates having between about 8 and 22 carbons, such as tridecyl alcohol ethoxylates, trimethylnonanyl ethoxylates, and isodecyl alcohol ethoxylates, isotridecyl alcohol ethoxylates; nonionic esters, alcohol, glycerol, and glycol esters, polyethylene glycol (PEG) esters such as diethylene glycol monostearates, glycerol monostearates, PEG laurates, PEG dilaurates, PEG monooleates, and PEG dioleates, wherein PEG has a molecular weight ranging between about 100 and 1000; ethoxylated acids and oils, including derivatives of castor oil, oleic acid, linoleic acid, myristic acid, lauric acid, and stearic acid, among others, where the organic acids have from between about 6 to 20 carbons having linear and branched chain structures, and degrees of ethoxylation from 1.5 to 200; alkyl polyglucoside surfactants having between about 1 and 10 saccharide units and an alkyl substitution from between about 0.5 and 2.5; low foaming surfactants, including ethylene oxide/propylene oxide (EO/PO) block copolymers, linear alcohol EO/PO, branched alcohol EO/PO, and linear alcohol EO with a chlorine cap. Preferred nonionic surfactants for use in the compositions and methods of the present invention are linear or branched alcohol ethoxylates and alkyl polyglucosides.

The surfactant concentration can be from 0.001, 0.01, 0.05, or 0.1% w/w and less than or equal to 20, 10, 5, 3, 2, 1, 0.75 or 0.5% w/w. In certain embodiments, the surfactant concentration is from 0.001 to 20% w/w, 0.01 to 5% w/w, from 0.1 to 4% w/w, from 0.2 to 3% w/w, or from 0.3 to 2% w/w.

At least one hydrogen peroxide stabilizer or chelating agent may be included to ensure that adequate levels of hydrogen peroxide in solution are maintained over time thereby prolonging shelf-life. A non-limiting list of suitable hydrogen peroxide stabilizers are 1-hydroxyethylidene-1,1,-diphosphonic acid (HEDP), amino tri(methylene phosphonic acid) (ATMP), diethylenetriamine penta(methylene phosphonic acid), 2-hydroxy ethylimino bis(methylene phosphonic acid), and ethylene diamine tetra(methylene phosphonic acid) (EDTMPA). Other peroxide stabilizers such as ethylenediaminetetraacetic acid (EDTA), diethylenetriaminepentaacetic acid (DTPA), N-(2-hydroxyethyl)-ethylenediaminetriacetic acid (HEDTA), nitrilotriacetic acid (NTA), 2-hydroxyethyliminodiacetic acid, ethylenediamine \N,N'-disuccinic acid, ethanoldiglycines, methylglycinediacetic acid (MGDA), propylenediamine tetraacetic acid (PDTA), ([S,S']-Ethylenediaminedisuccinic acid (EDDS), benzoic acid, salicylic acid, aminobenzoic acid, and citric acid. Hydrogen peroxide stabilizers can be present in a concentration of from 0.005, 0.01, 0.05, or 0.1% w/w and less than or equal to 20, 10, 5, 4, 3 or 2% w/w.

If it is desired to increase residence time on a surface (especially vertical or inclined surfaces) an effective amount of at least one thickening agent, that does not decompose in the presence of hydrogen peroxide, can be added to increase the viscosity of solutions according to the invention. Thickening agents which can be used in the present invention include, but are not limited to, cross-linked polyacrylates such as CARBOPOL™ (polymers available from Goodrich); polymeric carboxylates including modified and unmodified starches, xanthan gum (e.g. KELTROL 630™), and cellulose derivatives (e.g. NATROSOL 250™). The thickening agent can be present in a concentration of from 0.1, or 0.2% w/w, and less than or equal to 5, 2, 1, or 0.8% w/w. In certain embodiments, the thickening agent is present in a concentration of from 0.01 to 5% w/w, 0.05 to 5% w/w, from 0.1 to 5, or from 0.1 to 2% w/w.

The amount of thickening agent is selected to provide a solution of the desired viscosity. It will be appreciated by the person skilled in the art that the solution will work over a wide viscosity range, depending on the application. For example, solutions according to the invention can have a viscosity of from about 10, 15, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 centipoise. Solutions according to the invention can be in the form of gels having a viscosity of from 1400 to 1800 centipoise.

The desired pH is less than or equal to 4, 3.5, 3, 2.5, or 2 and from 0.5, 1, 1.5, 2, 2.5, or 3. In some embodiments, the pH is from 0.5 to 4, 1.5 to 4, or from 2 to 3. pH buffers or adjusters may be included in aqueous solutions to achieve the desired pH. Examples of these ingredients include NaOH, KOH, HCl, phosphoric acid, organic acids and mixtures thereof. Suitable organic acids for use herein include monocarboxylic acids, dicarboxylic acids and tricarboxylic acids or mixtures thereof, including acetic acid, citric acid, malonic acid, maleic acid, malic acid, lactic acid, glutaric acid, glutamic acid, aspartic acid, methyl succinic acid, succinic acid and mixtures thereof.

Skin conditioning agents or emollients can be used to prevent or reduce skin irritation when the composition comes in contact with skin. Examples include glycerin, sorbitol, cetyl alcohol, and allantoin. In one embodiment, the solution is no more than slightly irritating as determined according to the Acute Dermal Irritation/Corrosion test set forth in OECD Guideline for the Testing of Chemicals, Section 404, 2002.

Corrosion inhibitors are of benefit if the present inventive composition is to be used on metals, such as brass, copper or mild steel, to prevent or reduce corrosion thereof. Non-limiting examples of corrosion inhibitors are sodium nitrite, sodium molybdate, tolytriazoles and benzotriazoles.

Compositions according to the invention can be used to inactivate various microorganisms. Certain embodiments of the invention are effective even against bacterial and fungal spores, such as those that may be present on toilets, sinks and commodes (e.g. *Clostridium Difficile*).

The antimicrobial compositions of the invention can be used for a variety of domestic or industrial applications, e.g. to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g. floors, walls, windows, sinks, tables, counters and signs), eating utensils, hard-surface medical or surgical instruments and devices, and hard-surface packaging. Such hard surfaces can be made from a variety of materials comprising, for example, ceramic, metal, glass, wood or hard plastic. Suitable soft surfaces include, for example paper, filter media, hospital and surgical linens and garments, soft-surface medical or surgical instruments and devices, soft-surface packaging, food and skin. Certain soft surfaces can be made from a variety of materials comprising, for example, paper, fiber, woven or non-woven fabric, soft plastics and elastomers. When used on skin, the invention preferably includes skin conditioning agents or emollients.

The antimicrobial compositions can also be used in veterinary products such as products for sanitizing or disinfecting animal enclosures, pens, watering stations, and veterinary treatment areas such as inspection tables and operation rooms.

The invention also provides a method of antimicrobial treatment of a surface contaminated with a microorganism comprising applying to the surface a solution according to the present invention for a contact time of from 1 to 30 minutes. The microorganism can be a bacterial or fungal spore (e.g. *C. Difficile*). The antimicrobial solutions according to the invention can be applied to surfaces using a variety of methods. For example, the solutions can be sprayed or wiped onto the surface, they can be caused to flow over the surface, or the surface can be dipped into the solution.

EXAMPLES

The invention is further illustrated by the following non-limiting examples.

The bactericidal, fungicidal and sporicidal activities of various test solutions were evaluated by using the quantitative carrier test method (QCT-1) ASTM E2111, entitled "Standard Quantitative Carrier Test Method to Evaluate the Bactericidal, Fungicidal, Mycobactericidal and Sporicidal Potencies of Liquid Chemical Germicides." For virucidal testing, the method set forth in ASTM E1053, entitled "Standard Test Method for Efficacy of Virucidal Agents Intended for Inanimate Environmental Surfaces" was used.

A description of some of the ingredients used in the following examples is provided below to assist in understanding the invention.

DI water is deionized water.

Hydrogen peroxide is a 50% w/w technical grade commercial solution manufactured or sold by Degussa.

Hydrogen Peroxide Stabilizers

BRIQUEST ADPA-60AW™: 1-hydroxyethylidene bisphosphonic acid, manufactured or sold by Rhodia as a 60% w/w solution.

BRIQUEST 301-50A™: nitrilotris (methylenephosphonic acid), manufactured or sold by Rhodia as a 50% w/w solution.

EDTA: ethylenediaminetetraacetic acid.

NTA: nitrilotriacetic acid.

Surfactants

AMPHOSOL CG™: cocamidopropyl betaine, manufactured or sold by Stepan as a 30% w/w solution.

BIOSOFT S-101™: dodecyl benzene sulfonic acid, manufactured or sold by Stepan as a 96% w/w solution.

BIOTERGE PAS-8S™: sodium capryl sulfonate, manufactured or sold by Stepan as a 40% w/w solution.

ETHAL OA 23™: oleyl ($C_{18}$) alcohol ethoxylate, 23 moles of EO/mole of alcohol, manufactured or sold by Ethox Company as a 70% w/w solution.

GLUCOPON 425N™: alkyl polyglucoside, manufactured or sold by Cognis as a 50% w/w solution.

DOWFAX™ Hydrotrope: $C_6$ alkylated sulfonated diphenyl oxide disodium salt, manufactured or sold by Dow Chemical Company as a 45% w/w solution.

Thickening Agents

KELTROL T630™: xanthan gum (polysaccharide) manufactured or sold by Pkelco Company.

NATROSOL 250™: hydroxyethylcellulose, manufactured or sold by Hercules Incorporated.

Phosphoric acid is used as a pH buffer in the below experiments. All tests were performed at room temperature (20±2° C.).

Solutions 1-5

Solutions 1 to 5 were prepared and are summarized in Table 1. All solutions are in accordance with the present invention.

TABLE 1

| Ingredient | 1 % w/w | 2 % w/w | 3 % w/w | 4 % w/w | 5 % w/w |
|---|---|---|---|---|---|
| DI water | Qs to 100 | Qs to 100 | Qs to 100 | Qs to 100 | Qs to 100 |
| Keltrol T630 | 0.08 | 0 | 0 | 0.5 | 0 |
| Natrosol 250 | 0 | 0 | 0.5 | 0 | 0 |
| Briquest ADPA-60AW | 0.9 | 0 | 0 | 0.9 | 0 |
| Briquest 301-50A | 0 | 0 | 0 | 0 | 1.25 |
| NTA | 0 | 0.6 | 0 | 0 | 0 |
| EDTA | 0 | 0 | 0.7 | 0 | 0 |
| phosphoric acid | 0.11 | 0.19 | 0 | 0.11 | 0 |
| Biosoft S-101 | 0.18 | 0.14 | 0 | 0.18 | 0 |
| Bioterge PAS-8S | 0 | 0 | 0.16 | 0 | 0 |
| Dowfax Hydrotrope | 1.0 | 0.4 | 0 | 1.0 | 0 |
| Glucopon 425N | 0 | 0.2 | 0 | 0 | 0 |
| Ethal OA-23 | 0.08 | 0 | 0.07 | 0.08 | 0 |
| Amphosol CG | 0 | 0 | 0 | 0 | 0.15 |
| benzyl alcohol | 3.50 | 2.5 | 1.0 | 3.5 | 2 |
| hydrogen peroxide | 4.5 | 4 | 3.5 | 4.5 | 5 |
| glycolic acid | 1.3 | 2.25 | 1.5 | 1.3 | 1 |
| pH (using KOH) | 2.5 | 1.5 | 3.0 | 2.6 | 4 |
| Total | 100 | 100 | 100 | 100 | 100 |

Antimicrobial Test for Solution 1

Solution 1 was tested for its bactericidal, fungicidal and sporicidal activity using the QCT-1 method and for virucidal activity using the ASTM E1053 method and the results are presented in Table 2.

TABLE 2

| Test Organism | Contact time (minutes) | CFU/Control Carrier | CFU/Test Carrier | $Log_{10}$ Reduction |
|---|---|---|---|---|
| Staphylococcus aureus | 1 | $1.00 \times 10^6$ | 0 | 6.03 |
| Pseudomonas aeruginosa | 1 | $2.64 \times 10^6$ | 0 | 6.42 |
| Salmonella choleraesius | 1 | $8.17 \times 10^6$ | 0 | 6.91 |
| Spores of Bacillus subtilis | 10 | $1.05 \times 10^7$ | $1.18 \times 10^1$ | 6.05 |
| Spores of Clostridium sporogenes | 10 | $1.11 \times 10^7$ | 0 | 7.05 |
| Spores of Clostridium difficile | 10 | $8.03 \times 10^7$ | 0 | 7.90 |
| T. mentagrophytes | 10 | $3.90 \times 10^5$ | 0 | 5.55 |
| Polio virus | 1 | $2.76 \times 10^5$ | 0 | 5.69 |

CFU = colony forming units

Peroxide Stability Test for Solution 1

Solution 1 was tested for its peroxide stability using a seven day accelerated stability test method at 70° C. which correlates to storage of Solution 1 for one year at room temperature. Solution 1 showed less than 20% hydrogen peroxide loss at the end of the test.

Acute Dermal Irritation/Corrosion Test of Solution 4

Solution 4 was tested for its dermal irritation or corrosion on rabbits as per the OECD Guideline for the Testing of Chemicals, Section 404, 2002. The degree of irritancy was evaluated using the scoring system described in the "OECD Guideline for the Testing of Chemicals", Section 404, (OECD, 2002). According to these tests, Solution 4 was only slightly irritating in accordance with the Dermal Classification System used.

Solutions 6-10—Sporicidal Tests

Solutions 6 to 10 were prepared and tested against *B. subtilis* spores using the QCT-1 method and a contact time of 10 minutes. Of these solutions, only Solution 6 is in accordance with the present invention. These solutions and the results of the tests are summarized in Table 3 below.

TABLE 3

| Ingredient | 6 % w/w | 7 % w/w | 8 % w/w | 9 % w/w | 10 % w/w |
|---|---|---|---|---|---|
| DI water | Qs to 100 | Qs to 100 | Qs to 100 | Qs to 100 | Qs to 100 |
| Dowfax Hydrotrope | 0 | 0.4 | 0.4 | 0.4 | 0.4 |
| Briquest ADPA-60AW | 0.9 | 0.9 | 0.9 | 0.9 | 0.9 |
| phosphoric acid | 0.11 | 0.11 | 0.11 | 0.11 | 0.11 |
| Biosoft S-101 | 0.18 | 0.18 | 0.18 | 0.18 | 0.18 |
| Ethal OA-23 | 0.08 | 0.08 | 0.08 | 0.08 | 0.08 |
| hydrogen peroxide | 4 | 7 | 6.7 | 6.7 | 6.7 |
| glycolic acid | 1.3 | 0 | 0 | 0 | 0 |
| benzyl alcohol | 2 | 0 | 0 | 0 | 0 |
| pH (using KOH) | 2.5 | 0.7 | 1.5 | 2.0 | 2.5 |
| Total | 100 | 100 | 100 | 100 | 100 |
| Log reduction at 10 min. against *B. subtilis* spores (QCT-1 method) | 7.02 | TNTC | TNTC | TNTC | TNTC |

TNTC = colony forming units were too numerous to count

Solutions 11 and 12—Sporicidal Tests

Solutions 11 and 12 were prepared and tested against *B. subtilis* spores using the QCT-1 method and a contact time of 10 minutes. Solution 11 is in accordance with the present invention. Solution 12 is identical to Solution 11 except that glycolic acid is omitted. Thus, Solution 12 is not in accordance with the present invention. These solutions and the results of the tests are summarized in Table 4 below.

TABLE 4

| Ingredient | 11 % w/w | 12 % w/w |
|---|---|---|
| DI water | Qs to 100 | Qs to 100 |
| Dowfax Hydrotrope | 0.4 | 0.4 |
| Keltrol T630 | 0.5 | 0.5 |
| Briquest ADPA-60AW | 0.9 | 0.9 |
| phosphoric acid | 0.11 | 0.11 |
| Biosoft S-101 | 0.18 | 0.18 |
| Ethal OA-23 | 0.08 | 0.08 |
| Hydrogen peroxide | 4 | 4 |
| glycolic acid | 1.2 | 0 |
| benzyl alcohol | 3 | 3 |
| pH (using KOH) | 2.5 | 2.5 |
| Total | 100 | 100 |
| Log reduction at 10 min. against *B. subtilis* spores (QCT-1 method) | 7.17 | TNTC |

TNTC = colony forming units were too numerous to count

Solutions 13 to 19—Sporicidal Tests

Solutions 13 to 19 were prepared and tested against *B. subtilis* spores using the QCT-1 method at a contact time of 10 minutes. These solutions and the results of the tests are summarized in Table 5 below. Of these solutions, only Solution 19 is in accordance with the present invention.

TABLE 5

| Ingredient | 13 % w/w | 14 % w/w | 15 % w/w | 16 % w/w | 17 % w/w | 18 % w/w | 19 % w/w |
|---|---|---|---|---|---|---|---|
| DI water | | | | 82.51 | | | |
| Keltrol T630 | | | | 0.08 | | | |
| Briquest ADPA-60AW | | | | 1 | | | |
| phosphoric acid | | | | 0.11 | | | |
| Biosoft S-101 | | | | 0.18 | | | |
| Dowfax Hydrotrope | | | | 0.4 | | | |
| Ethal OA-23 | | | | 0.08 | | | |
| Hydrogen peroxide | 4.5 | 0 | 4.5 | 4.5 | 0 | 0 | 4.5 |
| benzyl alcohol | 0 | 2 | 2 | 0 | 2 | 0 | 2 |
| glycolic acid | 1.3 | 1.3 | 0 | 0 | 0 | 1.3 | 1.3 |
| pH | | | | 2.6 | | | |
| Log reduction at 10 min., against *B. subtilis* spores (QCT I method) | 0.92 | almost 0 | 0.81 | 0.8 | almost 0 | almost 0 | 7.25 |

Solution 20—Sporicidal Test

Solution 20, in accordance with a further embodiment of the invention, was prepared and tested against *B. subtilis* spores using the QCT-1 method at a contact time of 10 minutes. This solution and the results of the test are summarized in Table 6 below.

TABLE 6

| Ingredient | 20 % w/w |
|---|---|
| DI water | Qs to 100 |
| Keltrol T630 | 0.5 |
| Briquest ADPA-60AW | 0.9 |
| phosphoric acid | 0.11 |
| Biosoft S-101 | 0.18 |
| Ethal OA-23 | 0.08 |
| glycolic acid | 1.3 |
| hydrogen peroxide | 4 |
| benzyl alcohol | 3 |
| Dowfax Hydrotrope | 0.8 |
| pH (using KOH) | 2.5 |
| Log reduction, *B. subtilis* spores, 10 min, QCT-1 method | >6 |

The viscosity of Solution 20 was measured using a Brookfield viscometer, model LVT, with spindle #2 and at an RPM of 12. The results are summarized in Table 7 below.

TABLE 7

| Days | Viscosity (cp) |
|---|---|
| 0 | 1525 |
| 19 | 1525 |
| 29 | 1525 |
| 50 | 1512.5 |
| 75 | 1487.5 |
| 98 | 1475 |
| 130 | 1462.5 |

The results show that the viscosity of Solution 20 was maintained substantially constant over the 130 day test period.

Solutions 21-24—Sporicidal Tests

Solutions 21 to 24, all in accordance with the present invention, were prepared and tested against *B. subtilis* spores using the QCT-1 method at a contact time of 10 minutes. These solutions and the results of the test are summarized in Table 8 below.

TABLE 8

| Ingredients | 21 % w/w | 22 % w/w | 23 % w/w | 24 % w/w |
|---|---|---|---|---|
| DI water | qs to 100 | qs to 100 | qs to 100 | qs to 100 |
| Briquest ADPA 60-AW | 0.6 | 0.6 | 0.6 | 0.6 |
| Phosphoric acid | 0.11 | 0.11 | 0.11 | 0.11 |
| Benzyl alcohol | 3.5 | 3.5 | 3.5 | 3.5 |
| Hydrogen peroxide | 4.5 | 4.5 | 4.5 | 4.5 |
| Glycolic acid | 1.3 | 1.3 | 1.3 | 1.3 |
| Biosoft S101 | 0.18 | 0 | 0.18 | 0 |
| Ethal 23-OA | 0 | 0 | 0.05 | 0 |
| Dowfax Hydrotrope | 0 | 0 | 0.4 | 0.4 |
| pH | 2.6 | 2.64 | 2.65 | 2.75 |
| Log reduction, *B. subtilis* spores, 10 min. QCT-1 method. | 6.99 | 6.99 | 6.99 | 6.99 |

Solutions 25-27—Sporicidal Tests

Solutions 25 to 27 were prepared and tested against *B. subtilis* spores using the QCT-1 method at a contact time of 10 minutes. These solutions and the results of the test are summarized in Table 9 below. Of these solutions, only Solution 27 is in accordance with the present invention. Solution 27 contains phenoxyethanol, hydrogen peroxide, and glycolic acid in combination with other ingredients. Solutions 25 and 26 do not contain glycolic acid.

TABLE 9

| Ingredients | 25 % w/w | 26 % w/w | 27 % w/w |
|---|---|---|---|
| DI water | qs to 100 | qs to 100 | qs to 100 |
| Biosoft S101 | 0.18 | 0.18 | 0.18 |
| Ethal OA-23 | 0.08 | 0.08 | 0.08 |
| Briquest ADPA 60-AW | 0.6 | 0.6 | 0.6 |
| Phosphoric acid | 0.11 | 0.11 | 0.11 |
| Hydrogen peroxide | 4.5 | 4.5 | 4.5 |
| Phenoxyethanol | 2 | 0 | 2 |
| Benzyl alcohol | 0 | 2 | 0 |
| Lactic acid | 1.6 | 1.6 | 0 |
| Glycolic acid | 0 | 0 | 1.3 |
| pH | 2.7 | 2.7 | 2.7 |
| Log reduction, *B. subtilis* spores, 10 min. QCT-1 method. | <1 | <1 | 4.16 |

As can be seen from the above experiments, solutions comprising hydrogen peroxide, glycolic acid, and at least one of benzyl alcohol and phenoxyethanol provide a high rate of microbial kill. Certain embodiments are also effective as sporicides. Other solutions tested, that were not in accordance with the present invention, failed to achieve a high log reduction in colony forming units.

It will be appreciated that various modifications to the embodiments of the invention described above can be made, having regard to the teachings of the present specification. The invention is defined by the following claims and should not be limited to the specifically described embodiments.

The invention claimed is:

1. An antimicrobial solution having a pH from 0.5 to 4 and consisting of:
   a. from 3 to 8% w/w hydrogen peroxide;
   b. from 0.1 to 6% w/w of glycolic acid;
   c. from 2 to 4% w/w of benzyl alcohol
   d. optionally, from 0.001 to 5% w/w of at least one nonionic surfactant;
   e. optionally, from 0.01 to 5% w/w of a thickening agent;
   f. optionally, from 0.005 to 20% w/w of a hydrogen peroxide stabilizer;
   g. optionally, a pH adjuster in an amount sufficient to adjust the pH to within the range of 0.5 to 4;
   h. optionally, from an effective amount of at least one ingredient chosen from skin conditioning agents, builders, fragrances, dyes, corrosion inhibitors, additional antimicrobial agents, additional solvents, radical scavengers, soil suspenders, and dye transfer agents; wherein element h. excludes an anionic surfactant;
   i. optionally, an effective amount of an amphoteric surfactant, wherein the concentration of all surfactants does not exceed 20% w/w; and
   j. water q.s. to 100% w/w.

2. The solution of claim 1, wherein the glycolic acid is present in a concentration of from 0.1 to 5% w/w.

3. The solution of claim 1, having a pH of from 2 to 3, and wherein hydrogen peroxide is present in a concentration of from 4 to 7°A) w/w, glycolic acid is present in a concentration of from 1 to 1.5% w/w, and benzyl alcohol is present in a concentration of from 2 to 4% w/w.

4. The solution of claim 1, having a pH of from 1.5 to 4, and wherein hydrogen peroxide is present in a concentration of from 4 to 7 w/w, glycolic acid is present in a concentration of from 0.5 to 5% w/w, and benzyl alcohol is present in a concentration of from 2 to 4% w/w.

5. The solution of claim 1, wherein the at least one nonionic surfactant is present in a concentration of 0.01 to 5% w/w.

6. The solution of claim 1, wherein the thickening agent is present in a concentration of from 0.01 to 5% w/w.

7. A concentrated solution which can be diluted with water to form an antimicrobial solution having a pH from 0.5 to 4 and consisting of:
   a. from 3 to 8% w/w hydrogen peroxide;
   b. from 0.1 to 6% w/w of glycolic acid;
   c. from 2 to 4% w/w of benzyl alcohol;
   d. optionally, from 0.001 to 5% w/w of at least one nonionic surfactant;
   e. optionally, from 0.01 to 5% w/w of a thickening agent;
   f. optionally, from 0.005 to 20% w/w of a hydrogen peroxide stabilizer;
   g. optionally, a pH adjuster in an amount sufficient to adjust the pH to within the range of 0.5 to 4;
   h. optionally, an effective amount of at least one ingredient chosen from skin conditioning agents, builders, fragrances, dyes, corrosion inhibitors, additional antimicrobial agents, additional solvents, radical scavengers, soil suspenders, and dye transfer agents; wherein element h. excludes an anionic surfactant;
   i. optionally, an effective amount of an amphoteric surfactant, wherein the concentration of all surfactants does not exceed 20% w/w; and
   j. water q.s. to 100% w/w.

8. A disinfecting wipe comprising the solution of claim 1 embedded in a textile medium.

9. A method of antimicrobial treatment of a surface contaminated with a microorganism comprising applying to the surface the solution of claim 1 for a contact time of from 1 to 30 minutes.

10. A method of antimicrobial treatment of a surface contaminated with bacterial or fungal spores comprising applying to the surface the solution of claim 1 for a contact time of from 1 to 30 minutes.

11. A method of antimicrobial treatment of a surface contaminated with *C. difficile* comprising applying to the surface the solution of claim 1 for a contact time of from 1 to 30 minutes.

* * * * *